United States Patent
Chretien et al.

(10) Patent No.: US 10,766,848 B2
(45) Date of Patent: Sep. 8, 2020

(54) USE OF POLYMERIZATION INHIBITOR COMPOSITIONS

(71) Applicant: RHODIA OPERATIONS, Paris (FR)

(72) Inventors: Christelle Chretien, Bensalem, PA (US); Karel Vits, Shanghai (CN); Lars Fischer, Vienne (FR); Yan Shi, Shanghai (CN)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 15/757,497

(22) PCT Filed: Sep. 7, 2015

(86) PCT No.: PCT/CN2015/089016
§ 371 (c)(1),
(2) Date: Mar. 5, 2018

(87) PCT Pub. No.: WO2017/041204
PCT Pub. Date: Mar. 16, 2017

(65) Prior Publication Data
US 2019/0023641 A1  Jan. 24, 2019

(51) Int. Cl.
*C07C 67/62* (2006.01)

(52) U.S. Cl.
CPC .................. *C07C 67/62* (2013.01)

(58) Field of Classification Search
CPC .............................. C07C 67/62; C07C 69/54
See application file for complete search history.

(56) References Cited

U.S. PATENT DOCUMENTS

| | | | |
|---|---|---|---|
| 5,650,072 A | 7/1997 | McClain et al. | |
| 7,880,029 B2 | 2/2011 | Link et al. | |
| 8,067,629 B2 | 11/2011 | Tong | |
| 2003/0018217 A1 | 1/2003 | Dupont et al. | |
| 2006/0142613 A1 | 6/2006 | Yada et al. | |
| 2007/0078207 A1 | 4/2007 | Jonn et al. | |
| 2009/0203938 A1* | 8/2009 | Croizy ............... B01F 17/0064 562/600 |
| 2009/0234161 A1 | 9/2009 | Paul | |

FOREIGN PATENT DOCUMENTS

| | | |
|---|---|---|
| CN | 1111605 A | 11/1995 |
| CN | 1240205 A | 1/2000 |
| CN | 103214610 A | 7/2013 |
| EP | 0765856 A1 | 4/1997 |
| EP | 1273565 A1 | 1/2003 |
| EP | 1805128 B1 | 7/2008 |
| GB | 2285983 A | 8/1995 |
| JP | H05140027 A2 | 6/1993 |
| WO | 2013026729 A1 | 2/2013 |
| WO | WO2013026729 * | 2/2013 |

OTHER PUBLICATIONS

Lartigue-Peyrou (The use of phenolic compounds as a free-radical polymerization inhibitors, pp. 489-505, published 1996) (Year: 1996).*
WO2013026729 translated (Year: 2013).*
Gala et al. (Journal of Developing Drugs, Pharmaceutical Applications of Eutectic Mixtures, pp. 1-2, Published 2013) (Year: 2013).*
Shou-Ming Hwang, Ming-Jer Lee, Ho-Mu Lin, Fluid phase Equilibria 172 (2000), 183-196.

* cited by examiner

*Primary Examiner* — Jafar F Parsa
*Assistant Examiner* — Blaine G Doletski
(74) *Attorney, Agent, or Firm* — Osha Liang LLP

(57) ABSTRACT

The present invention relates to the use of at least two phenol derivatives jointly with at least one ancillary polymerization inhibitor which is different from these two phenol derivatives and particularly is selected from phenol derivatives, amine derivatives, thiazine derivatives, nitroso compounds, N-oxyl derivatives, metal salts, quinone derivatives, and mixtures thereof, to inhibit the polymerization of ethylenically unsaturated monomers comprising at least one heteroatom, it being also possible for a dispersant to be incorporated. The present invention also relates to a corresponding polymerization-inhibiting composition and to the corresponding process for preparing ethylenically unsaturated monomers comprising at least one heteroatom, and particularly acrylic monomers.

10 Claims, No Drawings

USE OF POLYMERIZATION INHIBITOR COMPOSITIONS

This application is a U.S. national stage entry under 35 U.S.C. § 371 of International Application No. PCT/CN2015/089016 filed 7 Sep. 2015, the entire disclosure of this application is hereby incorporated herein by reference.

The present invention relates to the field of the industrial preparation of ethylenically unsaturated monomers comprising at least one heteroatom, such as acrylic monomers.

Ethylenically unsaturated monomers have the property of undergoing spontaneous polymerization, more particularly under the effect of heat. This polymerization proves disruptive during monomer preparation steps, particularly during the manufacture, purification, and storage of said monomers. Unless it is prevented, it gives rise to detrimental yield losses. Frequent stops for plant maintenance are then necessary, in order to remove the deposits formed, and the production capacities are therefore reduced as a result, and in that case an extra production cost is incurred.

For example, the preparation of acrylic acid or acrylic esters from acrylic acid conventionally requires a distilling operation for the purposes of separating, concentrating, or purifying the monomer in question. Acrylic acid, however, when taken to a higher temperature, like that required for a distillation, exhibits a tendency to polymerize. The polymeric material thus formed, in liquid phase or vapor phase, then undergoes deposition on the various pieces of equipment employed for the process, and more particularly on the walls of the columns, on the plates, and on the condensers. The result of this is fouling of this equipment with, for example, substantial pressure losses in the distillation columns.

Solutions have already been proposed to combat this phenomenon of premature polymerization, particularly during distillations. It is in this vain that polymerization inhibitors are commonly employed. These are, most frequently, phenol derivatives, amine derivatives, thiazine derivatives, nitroso derivatives, and N-oxyl derivatives. Other polymerization inhibitors are also known, such as metal salts or else, particularly, quinone derivatives.

Preference, among these classes of polymerization inhibitors, is generally given to the use, on account of their enhanced effectiveness, of phenol derivatives such as, particularly, hydroquinone (HQ), 2,6-di-tert-butyl-paracresol (BHT), and 2,4-dimethyl-6-tert-butylphenol (Topanol A); amine derivatives such as phenylenediamine, thiazine derivatives such as, particularly, phenothiazine (PTZ) or methylene blue; nitroso compounds such as N-nitrosodiphenylamine; N-oxyl derivatives such as, for example, 2,2,6,6-tetramethyl-1-piperidine N-oxyl (TEMPO) and its derivatives: 4-hydroxy TEMPO (HTEMPO), 4-methoxy TEMPO, 4-oxo TEMPO, or 4-amino TEMPO; metal salts such as, for example, iron sulfate or a copper salt; or quinone derivatives such as para-benzoquinone or di-tert-butylbenzoquinone.

With a concern to have polymerization inhibitor systems of increased effectiveness available, moreover, proposals have already been made to combine some of the aforementioned inhibitors.

Accordingly, EP 765 856 describes the combined use of an N-oxyl derivative-type polymerization inhibitor with a phenol derivative-type polymerization inhibitor, with the aim of stabilizing acrylic acid during distillation or else during transport. EP 1 273 565 discloses the use of hydroquinone, Topanol A, BHT, and phenothiazine, either alone or in combination, for preventing the risk of polymerization in the distillation column during the synthesis and purification of (meth)acrylic anhydride.

Likewise in the context of the production of (meth)acrylic anhydrides, EP 1 805 128 describes the use of a polymerization inhibitor selected from the group consisting of (a) metal salts of thiocarbamic acid or dithiocarbamic acid and mixtures thereof with a phenol derivative or with phenothiazine and its derivatives, and (b) N-oxyl compounds in a mixture with 2,6-di-tert-butyl 4-methylphenol (BHT) alone or in the presence of 2,4-dimethyl 6-tert-butylphenol (Topanol A).

US 2006/0142613 describes the combined use of a phenol derivative and a copper-based polymerization inhibitor.

While these polymerization inhibitor systems do prove to be actually more satisfactory, they nevertheless remain capable of improvement. The reason is that, as is evident from the examples presented later on below, an inhibitor system combining a phenol derivative such as hydroquinone (HQ) with a thiazine derivative such as phenothiazine (PTZ) does not constitute a complete escape from the phenomenon of polymerization.

WO 2013/026729 discloses a process for preparing a pulverulent composition which has inhibitory properties by an isothermal cogranulating process. Said composition is different from a simple juxtaposition of the elementary solids. For example, said composition has a melting point different from the melting point of anyone of the elementary solids. In addition, said composition has its own specific X-Ray diffraction spectrum: its rays are not the rays of the X-Ray diffraction spectrum of the elementary compounds. Thus, this document discloses the use of a new compound as a polymerization inhibitor, but not the combined use of the elementary solids.

Furthermore, proposals have already been made, for enhancing the production of certain ethylenically unsaturated monomers, to add dispersants so as to disperse the fouling material originating from the unwanted polymerization and to prevent their deposition on plant surfaces, so as to obviate excessive and expensive maintenance operations.

Accordingly, U.S. Pat. No. 5,650,072 proposes the addition of a naphthalene sulfonate-formaldehyde condensate during the production of acrylonitrile in order to control fouling on the walls of industrial plants. Still within the context of acrylonitrile production, U.S. Pat. No. 8,067,629 describes the use of a styrene sulfonate polymer as a dispersant preventing the deposition of unwanted residues on the walls of industrial plants. Lastly, U.S. Pat. No. 7,880,029 describes the employment of N-alkylsuccinimide during the formation of acrylic monomers.

The specific aim of the present invention is to reinforce the effectiveness of the existing polymerization inhibitor systems, or to prevent the premature polymerization of ethylenically unsaturated monomers comprising at least one heteroatom during the production of said monomers, or, expressed alternatively, the stabilization of said monomers, or else to prevent the deposition of unwanted residues that may be formed on the internals of the plants. In other words, the present invention is directed to the overall improvement, particularly of the usage levels of equipment, in the industrial preparation of ethylenically unsaturated monomers comprising at least one heteroatom, via the synergistic means of inhibiting polymerization and reducing fouling. In the context of the present invention, the invention therefore aims to provide, generally speaking, "stabilizer systems" or else "inhibiting and/or stabilizing" systems. A combined solution of this kind had never been proposed in the past.

Therefore, according to one of its aspects, the present invention relates to the use of at least two phenol derivatives jointly with at least one ancillary polymerization inhibitor which is different from these two phenol derivatives and in particular is selected from phenol derivatives, amine derivatives, thiazine derivatives, nitroso compounds, N-oxyl derivatives, metal salts, quinone derivatives, and mixtures thereof, to inhibit the polymerization of ethylenically unsaturated monomers comprising at least one heteroatom, such as acrylic monomers.

According to one particular embodiment, the phenol derivatives are para-methoxyphenol (PMP) and pyrocatechol (PC).

Therefore, according to another of its aspects, the invention relates to the use of para-methoxyphenol (PMP) and pyrocatechol (PC), jointly with at least one ancillary polymerization inhibitor selected particularly from phenol derivatives, amine derivatives, thiazine derivatives, nitroso compounds, N-oxyl derivatives, metal salts, quinone derivatives, and mixtures thereof, to inhibit the polymerization of ethylenically unsaturated monomers comprising at least one heteroatom, such as acrylic monomers.

The use to which the present invention pertains is intended more particularly to limit and/or prevent fouling of industrial equipment used in the preparation of ethylenically unsaturated monomers comprising at least one heteroatom, and more particularly of purifying equipment and of peripheral equipment during purification of ethylenically unsaturated monomers comprising at least one heteroatom, such as acrylic monomers, and particularly during distillation.

The invention relates more particularly to the use of an effective amount of two phenol derivatives, particularly of para-methoxyphenol (PMP) and pyrocatechol (PC), to enhance the polymerization-inhibiting effectiveness of at least one ancillary polymerization inhibitor which is different from the two phenol derivatives, and particularly different from PMP and PC.

According to one particular embodiment, the two phenol derivatives may be employed jointly with para-dimethoxybenzene (PDMB).

According to one particular embodiment, a dispersant may be combined with the inhibitor systems employed in the aforementioned uses.

Therefore, according to another of its aspects, the present invention pertains to the use of at least one dispersant and of at least two phenol derivatives, particularly para-methoxyphenol (PMP) and pyrocatechol (PC), jointly with at least one ancillary polymerization inhibitor which is different from these two phenol derivatives and particularly different from para-methoxyphenol (PMP) and pyrocatechol (PC), and which more particularly is selected from phenol derivatives, amine derivatives, thiazine derivatives, nitroso compounds, N-oxyl derivatives, metal salts, quinone derivatives, and mixtures thereof, to inhibit the polymerization of ethylenically unsaturated monomers comprising at least one heteroatom, such as acrylic monomers.

The present invention is likewise directed to a process for preparing ethylenically unsaturated monomers comprising at least one heteroatom, particularly acrylic monomers, wherein said monomers are prepared, particularly distilled, in the presence of an effective amount, particularly for preventing their polymerization, of at least two phenol derivatives, and particularly of PMP and PC, and optionally of para-dimethoxybenzene (PDMB) and of at least one ancillary polymerization inhibitor which is different from the phenol derivatives, and particularly different from PMP and PC, and selected particularly from phenol derivatives, amine derivatives, thiazine derivatives, nitroso compounds, N-oxyl derivatives, metal salts, quinone derivatives, and mixtures thereof. The present invention likewise pertains to a polymerization-inhibiting composition comprising at least:
  (a) two phenol derivatives, and particularly para-methoxyphenol (PMP) and pyrocatechol (PC), and
  (b) at least one ancillary polymerization inhibitor which is different from the compounds (a) and particularly is (are) selected from phenol derivatives, amine derivatives, thiazine derivatives, nitroso derivatives, N-oxyl derivatives, metal salts, quinone derivatives, and mixtures thereof,
  (c) and optionally para-dimethoxybenzene (PDMB).

The present invention is also directed to a composition comprising at least
  (a) an ethylenically unsaturated monomer comprising at least one heteroatom, such as an acrylic monomer, optionally employed in a solvent,
  (b) two phenol derivatives, and particularly para-methoxyphenol (PMP) and pyrocatechol (PC), and
  (c) at least one, and preferably at least two, ancillary polymerization inhibitor(s) which is or are different from the compounds (b) and particularly is or are selected from phenol derivatives, amine derivatives, thiazine derivatives, nitroso derivatives, N-oxyl derivatives, metal salts, quinone derivatives, and mixtures thereof,
  (d) and optionally para-dimethoxybenzene (PDMB).

It should be noted that the inhibitor component (c) may also be present in the composition in the solute state, which means that it may be employed therein in a solvent. This solvent is generally different from the solvent considered with regard to the monomer component (a).

According to yet another of its aspects, the present invention concerns the use of at least one phenol derivative jointly with at least one dispersant, to increase the rate of use of equipment during the preparation of ethylenically unsaturated monomers comprising at least one heteroatom, such as acrylic monomers.

According to one particular embodiment of this last aspect, the phenol derivative is PMP.

The present invention is directed lastly to a process for preparing ethylenically unsaturated monomers comprising at least one heteroatom, particularly acrylic monomers, wherein said monomers are prepared, more particularly are distilled, in the presence of an effective amount of at least one phenol derivative and of at least one dispersant.

Ethylenically Unsaturated Monomers

In the context of the present invention, an ethylenically unsaturated monomer is a monomer comprising at least one ethylenic unsaturation. A heteroatom is any atom that is not carbon or hydrogen. Typical heteroatoms are nitrogen, oxygen, sulphur, phosphorus, chlorine, bromine, and iodine. Ethylenically unsaturated monomers comprising at least one heteroatom comprise, in particular, halogenated unsaturated monomers, acrylic monomers, unsaturated acrylic resins, unsaturated amides, unsaturated ethers, and vinylpyridines.

Halogenated unsaturated monomers include vinyl chloride, chloroprene, vinylidene chloride, vinylidene fluoride, vinyl fluoride and mixtures thereof.

Acrylic monomers include unsaturated acids typified by acrylic acid (AA), methacrylic acid (MAA), and crotonic acid; acrylates typified by methyl acrylate, ethyl acrylate, n-butyl acrylate, 2-ethylhexyl acrylate, hydroxyethyl acrylate, hydroxypropyl acrylate, dimethylaminomethyl acrylate, or any other acrylate derivative; methacrylates (MA), typified by methyl methacrylate, butyl methacrylate, lauryl methacrylate, dimethylaminoethyl methacrylate, and stearyl methacrylate; acrylonitrile (ACN), acrolein, acrylic anhydride, methacrylic anhydride and mixtures thereof.

Unsaturated acrylic resins include acrylated epoxy resins and polyethylene glycol diacrylate.

Unsaturated amides include acrylamide, N,N-dimethylacrylamide, methylenebisacrylamide, and N-vinylpyrrolidone.

Unsaturated ethers include vinyl methyl ether.

Other ethylenically unsaturated monomers comprising at least one heteroatom include, further, vinyl acetate, diethyl vinylphosphonate, styrenesulfonic acids and sodium styrenesulfonate.

According to one particular embodiment, the ethylenically unsaturated monomer comprising at least one heteroatom for stabilization may be selected from acrylic monomers.

Phenol Derivatives.

Representatives of phenol derivatives include, in particular, catechol or 1,2-dihydroxybenzene (PC), para-methoxyphenol or 4-methoxyphenol (PMP or MEHQ), hydroquinone (HQ), ortho methoxyphenol (guaiacol), 2,4-dimethyl-6-tert-butylphenol (Topanol A), phenol, cresol, catechol, 2,6-ditert-butyl-para-cresol or 2,6-di-tert-butyl-4-methylphenol (BHT), and 2,5-dibutyl-1-hydroxytoluene.

The total amount of the two phenol derivatives may be between 20 ppm and 1%, more particularly between 100 and 5000 ppm, and, for example, from 500 to 2000 ppm, by weight, relative to the total weight of the monomer to be stabilized against risk of polymerization.

In actual fact, the total amount of phenol derivatives is dependent on the ethylenically unsaturated monomer comprising at least one heteroatom for stabilization and also on the operating conditions to which this monomer is subject. More particularly, in an application of substantial temperatures, the amount will be higher, as may be the case during steps of distillative purification.

The at least two phenol derivatives and the ancillary inhibitor or inhibitors may be employed in a phenolic derivatives/ancillary inhibitor(s) weight ratio of from 90/10 to 10/90, particularly from 70/30 to 30/70, more particularly from 50/50 to 55/45.

The two phenol derivatives, and particularly para-methoxyphenol (PMP) and pyrocatechol (PC), may be employed with at least one ancillary polymerization inhibitor in a weight ratio of the first phenol derivative (PMP) to the second phenol derivative (PC) of from 1 to 99, more particularly from 1 to 45, especially from 2.5 to 20.

Ancillary Polymerization Inhibitor

Representatives of the various classes of polymerization inhibitors that may be employed in the traditional system of polymerization inhibitors are identified hereinafter.

For the purposes of the invention, the term "ancillary" signifies that the inhibitor so qualified is distinct from the phenol derivatives employed, and more particularly from para-methoxyphenol (PMP) and pyrocatechol (PC), where appropriate, as far as this particular embodiment is concerned.

The phenol derivatives, and more particularly para-methoxyphenol (PMP), and pyrocatechol (PC), are advantageously employed with at least one ancillary inhibitor, preferably at least two.

Where at least two distinct inhibitors are considered jointly with the two phenol derivatives, and more particularly with PC and PMP, this combination of two inhibitors may also be termed a polymerization inhibition system.

The one or more ancillary inhibitors are advantageously selected from the classes of thiazine derivatives, phenol derivatives, amine derivatives, nitroso derivatives, N-oxyl derivatives, metal salts, and quinone derivatives, provided they are different from the two phenol derivatives employed.

Representatives of thiazine derivatives include, particularly, phenothiazine (PTZ) or methylene blue.

Representatives of phenol derivatives include, particularly, catechol or 1,2-dihydroxybenzene (PC), para-methoxyphenol or 4-methoxyphenol (PMP or MEHQ), hydroquinone (HQ), ortho methoxyphenol (guaiacol), 2,4-dimethyl-6-tert-butylphenol (Topanol A), phenol, cresol, catechol, 2,6-ditert-butyl-para-cresol or 2,6-di-tert-butyl-4-methylphenol (BHT), and 2,5-dibutyl-1-hydroxytoluene.

Representatives of amine derivatives include, particularly, phenylenediamine or diethylhydroxylamine.

Representatives of nitroso compounds include, particularly, N-nitrosodiphenylamine or cupferron.

Representatives of N-oxyl derivatives include, particularly, 2,2,6,6 tetramethyl-1-piperidine N-oxyl (TEMPO) and its derivatives: 4-hydroxy TEMPO (HTEMPO), 4-methoxy TEMPO, 4-oxo TEMPO or 4-amino TEMPO, di-tert-butyl nitroxide, 2,2,5,5-tetramethyl-3-oxopyrrolidine-oxyl, 2,2,6,6-tetramethyl-4-acetoxypiperidine oxyl, and 4,4',4"-tris(2,2,6,6-tetramethylpiperidine-oxy)phosphate.

Representatives of metal salts include the metal salts of thiocarbamic or dithiocarbamic acid, salts of transition metals such as copper dibutyldithiocarbamate (CB), copper diethyldithiocarbamate, copper dimethyldithiocarbamate, or copper chloride, and manganese salts such as manganese acetate.

Representatives of quinone derivatives include para-benzoquinone, dimethylbenzoquinone, or di-tert-butylbenzoquinone.

The total amount of polymerization inhibitor, comprising the two phenol derivatives, and particularly PMP and PC, the ancillary inhibitor, and optionally PDMB, may be between 20 ppm and 1%, more particularly between 100 and 5000 ppm, and, for example, from 500 to 2000 ppm by weight, relative to the total weight of the monomer to be stabilized against risk of polymerization.

Dispersant

The term "dispersant" is used to name a component preventing deposits (particularly of polymers) and the fouling of industrial equipment, particularly of purifying equipment. Other terms may also be employed that are equivalent to the term "dispersant". They include, in particular: detergent, surfactant, antifouling additive, and antideposition agent.

The dispersant in the sense of the present invention may be composed of a mixture of two or more dispersants.

The classes of dispersants which may be employed in the context of the present invention are particularly as follows:
 sulfonates, such as styrenesulfonate, naphthalenesulfonate, for instance SUPRAGIL MNS/90, which is a polyalkylnaphthalenesulfonate sold by Solvay,
 esters, such as the methyl ester of salicylic acid, also called methyl salicylate,
 succinimides, such as polyisobutenylsuccinimide,
 tristyrylphenols, such as ethoxylated TSP and tristyrylphenol phosphate ethoxylate,
 acrylates, such as ethyl methacrylate, ethoxy methacrylate, and 2-ethylhexyl acrylate,
 amides, such as dimethylamides, acrylamides such as N-tert-butylacrylamide or N-(butoxymethyl)methacrylamide, amines, such as isopropylhydroxyl amine and Mannich bases, imidazoline, such as 1-aminoethyl-2-C17 alkylene-2-imidazoline, phenates, such as sulfurized calcium alkylphenate, phosphates, such as sodium polyphosphates such as the tripolyphosphate, phosphate esters, and ethoxylated phosphate esters, and mixtures thereof.

According to one particular embodiment, the dispersant may be polyalkylnaphthalenesulfonate, particularly that sold by SOLVAY under the name Supragil MNS/90.

All of these components may be in the form of monomers, polymers, or copolymers.

The total amount of dispersant may be between 10 ppm and 2%, more particularly between 50 ppm and 1%, and, for example, from 500 to 5000 ppm by weight, relative to the total weight of the ethylenically unsaturated monomer comprising at least one heteroatom.

In the embodiment which involves using at least one phenol derivative, possibly PMP, and at least one dispersant, the phenol derivative and the dispersant may be employed in a weight ratio of phenol derivative to dispersant of from 10/90 to 90/10, more particularly from 30/70 to 70/30, and, for example, from 50/50 to 45/55.

The increase in the rate of use of equipment via the polymerization-inhibiting activity and/or the antideposition effect may be desired in all industrial stages involving the use of ethylenically unsaturated monomers comprising at least one heteroatom. Mention may be made more particularly of the stages of purification or else the stages of manufacture, storage, transport, etc.

In the case of use in a purification step, the purifying equipment, and more particularly distilling equipment, for which the present invention proposes, more particularly, to control fouling of their walls and their internals may be, in particular, the distillation columns themselves, scrubbing columns, absorption columns, or else all of the peripheral equipment such as condensers, pumps, boilers, phase separators, and the associated piping. These inhibitor systems described in the context of the present invention may also be used in liquid/liquid extractions.

As will become apparent from the description of the particular embodiment of the invention, hereinbelow, in which the two phenol derivatives are para-methoxyphenol (PMP) and pyrocatechol (PC), the polymerization inhibition systems formed by the joint presence of two phenol derivatives and at least one ancillary inhibitor may be added entirely conventionally to the monomer to be stabilized. It is possible, moreover, to envisage the continuous or else repeated addition of said polymerization inhibition system over time, at one or more points of introduction. Furthermore, the addition of the phenol derivatives, the ancillary inhibitor(s), dispersants, and additives may be simultaneous or separate.

The details of implementation which are given hereinafter for this particular embodiment apply to the invention in its entirety.

Similarly, in the embodiments where the dispersant is present, it may be introduced simultaneously with the polymerization inhibition system, or else separately. As for the potential points of introduction, they are identical to those envisaged customarily for polymerization inhibitors.

Particular Embodiment: Para-Methoxyphenol (PMP) and Pyrocatechol (PC)

The inventors found, unexpectedly, that it is possible to simulate significantly the inhibitory effect on polymerization of a conventional inhibitor or inhibitor system, provided it is employed in a reaction medium comprising at least one ethylenically unsaturated monomer comprising at least one heteroatom, such as an acrylic monomer, with at least two phenol derivatives, and more particularly para-methoxyphenol (PMP) and pyrocatechol (PC). Against all expectation, the effectiveness of this conventional inhibitor or inhibitor system is found to be "boosted" or "doped" by the joint presence of these two phenol derivatives, and more particularly of para-methoxyphenol (PMP) and pyrocatechol (PC).

To the knowledge of the inventors, this advantageous effect of the combination of two phenol derivatives, and more particularly of the combination of para-methoxyphenol (PMP) and pyrocatechol (PC), on the inhibitory effect of a conventional system has never been described. It will be noted, moreover, that there is recognition that the effectiveness in terms of inhibiting polymerization of each of the two compounds PMP and PC, taken in isolation, is less than of the most widely used systems. Indeed, the phenol derivative pyrocatechol, and para-methoxyphenol, are already known as polymerization inhibitors. However, with regard to their reduced effectiveness, by comparison with that of the phenol derivatives discussed above, such as HQ, PTZ, or TEMPO, these two compounds are not conventionally employed as effective polymerization inhibitors.

The phenol derivative pyrocatechol (PC), considered more particularly in the context of the present invention, is likewise commonly identified as catechol or 1,2-dihydroxybenzene.

Para-methoxyphenol is also commonly identified as 4-methoxyphenol or PMP or MEHQ (hydroquinone methyl ether).

In the context of the embodiment in which PMP and PC are combined, para-methoxyphenol (PMP) and pyrocatechol (PC) are advantageously employed in a weight ratio of (PMP) to (PC) of from 1 to 99, more particularly from 1 to 45, and especially from 2.5 to 20.

The para-methoxyphenol (PMP), pyrocatechol (PC), and ancillary inhibitor(s) are advantageously employed in a weight ratio of (PMP)+(PC) to ancillary inhibitor(s) of from 0.002 to 500, especially from 0.1 to 20, more particularly from 0.25 to 10.

According to one variant embodiment, the PMP and PC are combined, furthermore, with para-dimethoxybenzene (PDMB).

The invention likewise relates to the use of:

(a) para-methoxyphenol (PMP) and pyrocatechol (PC), and (b) at least one polymerization inhibitor which is distinct from the compounds (a) and particularly is selected from phenol derivatives, amine derivatives, thiazine derivatives, nitroso compounds, N-oxyl derivatives, metal salts, quinone derivatives, and mixtures thereof, (c) and optionally para-dimethoxybenzene (PDMB), in a mixture for stabilization comprising at least one ethylenically unsaturated monomer comprising at least one heteroatom, such as an acrylic monomer, as a polymerization inhibition system.

The invention likewise pertains to a polymerization-inhibiting composition comprising para-methoxyphenol (PMP) and pyrocatechol (PC), and optionally para-dimethoxybenzene (PDMB).

According to one particular embodiment, a polymerization-inhibiting composition comprising PMP and PC and optionally PDMB, in accordance with the present invention, may have a PMP content of between 50% and 99% by weight, especially between 60% and 99% by weight, more particularly between 75% and 95% by weight, relative to the total weight of the composition.

The invention also extends to a polymerization-inhibiting composition comprising at least:

(a) para-methoxyphenol (PMP) and pyrocatechol (PC), and (b) at least one polymerization inhibitor different from the compounds (a) and selected particularly from phenol derivatives, amine derivatives, thiazine derivatives, nitroso derivatives, N-oxyl derivatives, metal salts, and quinone derivatives, (c) and optionally para-dimethoxybenzene (PDMB).

The invention is also directed to a composition comprising at least:

an ethylenically unsaturated monomer comprising at least one heteroatom, such as an acrylic monomer, a polymerization-inhibiting composition as defined above.

The compositions specified above may further comprise a dispersant as defined earlier. In that case, the polymerization-inhibiting composition may also be called a stabilizing composition.

Lastly, the invention is directed to a process for preparing ethylenically unsaturated monomers comprising at least one heteroatom, particularly acrylic monomers, employing a distillation of said monomers, wherein said monomers are distilled in the presence of an effective amount, particularly for preventing their polymerization, of para-methoxyphenol (PMP), pyrocatechol (PC), optionally para-dimethoxybenzene (PDMB), and at least one ancillary polymerization inhibitor which is different from the PMP and the PC, and selected particularly from phenol derivatives, amine derivatives, thiazine derivatives, nitroso compounds, N-oxyl derivatives, metal salts, quinone derivatives, and mixtures thereof.

The distillation temperatures at which equipment fouling is most particularly observed are commonly between 30 and 300° C., more particularly between 50 and 200° C. and, for example, between 70 and 160° C., particularly at a pressure of between 0 and 3 bar in absolute pressure, more particularly between 0.1 and 2 bar, and, for example, between 0.3 and 1.5 bar in absolute pressure, and in the presence of oxygen.

The invention therefore proves especially advantageous for these operating conditions.

The para-methoxyphenol (PMP), pyrocatechol (PC), ancillary polymerization inhibitor(s), and optionally para-dimethoxybenzene (PDMB) are advantageously employed in a total amount of from 20 ppm to 1%, as for example from 100 to 5000 ppm and preferably from 500 to 2000 ppm, relative to the total weight of the monomer for stabilization.

The inventors have demonstrated that a mixture of para-methoxyphenol (PMP) and pyrocatechol (PC) enhances the performance of existing polymerization inhibitor systems. As the examples hereinafter show, polymer deposits may be significantly reduced or even prevented both in the column and in the reaction flask in an operation simulating the industrial conditions for distillation of ethylenically unsaturated monomers comprising at least one heteroatom, such as acrylic monomers.

What is more, this "booster" or stimulatory effect that is observed enables the usual amount of ancillary polymerization inhibitor(s) to be decreased, with obvious advantages from the industrial standpoint.

Accordingly, in one advantageous variant embodiment, the total amount of PMP, PC, and ancillary polymerization inhibitor(s) may be adjusted to the conventionally employed amount of ancillary polymerization inhibitor(s) employed alone, i.e., without PMP and PC.

The total amount of PMP and PC may be between 20 ppm and 1%, more particularly from 100 to 5000 ppm and, for example, from 500 to 2000 ppm by weight, relative to the total weight of the monomer to be stabilized against risk of polymerization.

According to one particular embodiment, the PMP and PC may be combined with para-dimethoxybenzene (PDMB).

When present, the PDMB may have an amount of from 0% to 50%, more particularly from 2% to 25% by weight, relative to the total weight of PMP, PC, and PDMB.

As evident from the foregoing, another aspect of the invention relates to the use of an effective amount of para-methoxyphenol (PMP) and pyrocatechol (PC) to enhance the polymerization-inhibiting effectiveness of at least one ancillary polymerization inhibitor.

In the sense of the invention, this "effective amount" denotes the minimum amount of para-methoxyphenol (PMP) and pyrocatechol (PC) at which an improvement is observed in the polymerization inhibition exhibited by the ancillary inhibitor when it is combined with para-methoxyphenol (PMP) and pyrocatechol (PC), by comparison with the inhibition it exhibits in the absence of para-methoxyphenol (PMP) and pyrocatechol (PC).

As is evident from the foregoing, the para-methoxyphenol (PMP) and pyrocatechol (PC) may be combined with one or more ancillary polymerization inhibitors.

According to one particular embodiment of the present invention, the para-methoxyphenol (PMP) and pyrocatechol (PC) are employed with at least one phenol derivative, thiazine derivative, amine derivative, nitroso compound, N-oxyl derivative, metal salt, quinone derivative, or with a mixture thereof.

According to one even more particular embodiment, they are employed with one or more ancillary polymerization inhibitors comprising, or even consisting of, hydroquinone (HQ) and/or phenothiazine (PTZ), where appropriate in combination with copper derivatives.

According to yet another embodiment, the traditional system of polymerization inhibitors is free from a derivative of copper salts. Preference is generally given to this embodiment insofar as it removes the need for eliminating the residual traces of copper salts at the end of treatment. Accordingly, there is then no need to have suitable effluent treatment stations available, as is the case when such copper derivatives are used.

The PC, PMP, and, where appropriate, PDMB, further to one of the ancillary polymerization inhibitors in accordance with the invention, may be employed according to various modes of use, in line with the general knowledge of a person skilled in the art.

The PC, PMP, and, where appropriate, PDMB may be introduced independently of one another or in the form of a composition in accordance with the invention. They may therefore be formulated prior to their use.

This composition may be in a solid form after having been shaped by any of various methods: powders, flakes, prills, without limitation, and obtained by mixing or by co-generation of solids (crystallizing, flaking, atomizing, prilling, granulated, pelletizing, etc.).

This composition may alternatively be formulated with a solvent, and/or may be formulated with an amount of monomer in accordance with the monomer intended for treatment according to the invention.

It is also possible to consider the addition, to a mixture or a composition comprising PC, PMP, and, where appropriate, PDMB, of polymerization inhibitor(s) jointly considered, before it is employed in the mixture comprising the monomer for stabilization.

The person skilled in the art is able, on the basis of his or her knowledge, to give preference to one or other of these implementation variants.

The way in which these compounds, whether or not in the form of a mixture according to the invention, are introduced into the mixture comprising the monomer to be stabilized, and for example to be purified, is also within the competence of the person skilled in the art.

The inhibitors may therefore be introduced using appropriate injection nozzles.

By "mixture comprising the monomer for stabilization" is meant the whole of the phase as employed in the industrial preparation step in question—for example, at the start of a purification process, particularly distillation, particularly comprising the ethylenically unsaturated monomer or monomers comprising at least one heteroatom, such as the acrylic monomer or monomers, the polymerization inhibitors, and also any other additive there may be.

A composition in accordance with the invention, or the mixture for stabilization, for example for purification, may further comprise one or more additives selected from detergents other than the dispersants, antioxidants, antifoams, rust inhibitors, corrosion inhibitors, and surfactants distinct from the dispersants in accordance with the invention. The detergents distinct from the dispersants are advantageously selected from salicylates, phenates different from the dispersants, and sulfonates different from the dispersants. The antioxidants are advantageously selected from amines different from the dispersants, and derivatives of phenol. The antifoams are advantageously selected from silicones and acrylates. The rust inhibitors are advantageously selected form amines different from the dispersants, esters different from the dispersants, derivatives of phenol, and sulfonates different from the dispersants. The corrosion inhibitors are advantageously selected from nitrogen compounds such as triazoles and thiadiazoles.

The selection of these ancillary additives, and the adjustment of their respective amounts, is clearly part of the competence of a person skilled in the art.

Finally, in the context of the present invention and in the case of distillation, the mixture to be purified and/or the polymerization inhibitors in accordance with the invention may be introduced directly into the distillation column. The purification process, and particularly distillation process, may more particularly be a continuous process. In that case, the supplying of monomer(s) for purification and of polymerization inhibitors takes place continuously. The point at which the mixture for purification is introduced may vary according to the apparatus used. The selection of these parameters and of the apparatus is part of the general knowledge of a person skilled in the art and has no effect whatsoever on the technical effect considered in the context of the present invention.

When the inhibitor and/or stabilizer system in accordance with the present invention is used in the context of preparation of an ethylenically unsaturated monomer comprising at least one heteroatom, the inhibitor and/or stabilizer system may be removed at the end of the process by distillation, washing with sodium hydroxide solution, liquid-liquid extraction, or else by adsorption.

The examples which follow illustrate the invention but without limiting its scope.

EXAMPLES 1 TO 6

The effectiveness of inhibitor and/or stabilizer systems, in accordance with the invention or control systems, was validated in a reflux distillation test simulating a step of distillative purification of methyl methacrylate.

The apparatus used comprises a 100 ml round-bottom flask in glass, surmounted by a double-wall refrigerating column with spikes, with a height of 33 cm.

The inhibitors considered are as follows:
Hydroquinone sold by Solvay, referred to as HQ,
phenothiazine sold by Sigma-Aldrich, referred to as PTZ,
para-methoxyphenol sold by Solvay, referred to as PMP, and
pyrocatecol sold by Solvay, referred to as PC.
The dispersant used is as follows:
polyalkylnaphthalenesulfonate sold by Solvay under the name Supragil MNS/90.

For each of the tests, 50 ml of methyl methacrylate are introduced into the flask with the inhibitor system tested, when present. Table 1 below shows the nature of the compounds forming each system tested, and their respective weight proportions.

Distillation is carried out at 100° C. under atmospheric pressure for 48 hours.

The phenomenon of polymerization, where it occurs, is recorded by visual examination of the walls of the flask and of the refrigerating column. These observations are likewise reported in table 1 below.

TABLE 1

|  | Example 1 (comparative) | Example 2 (comparative) | Example 3 (comparative) | Example 4 (comparative) | Example 5 (Invention) | Example 6 (Invention) |
| --- | --- | --- | --- | --- | --- | --- |
| Inhibitor and/or stabilizer system Tested | WITHOUT | 100 ppm HQ and 100 ppm PTZ | 150 ppm HQ + 150 ppm PTZ | 100 ppm PMP + 100 ppm PC | 100 ppm HQ + 100 ppm PTZ + 100 ppm (PMP + PC) | 100 ppm HQ + 100 ppm PTZ + 50 ppm (PMP + PC) + 50 ppm Supragil MNS/90 |
| Observation after 48 h | Polymer deposits in the flask and column | Polymer deposits within the column | Polymer deposits within the column | Polymer deposits in the flask and column | No polymer deposit is observed either in the flask or within the column | No polymer deposit is observed either in the flask or within the column |

The results given above show that only the distillation of methyl methacrylate carried out in the presence of a polymerization stabilizer and/or inhibitor system in accordance with the invention completely removes the phenomenon of polymerization both in the flask and in the column. Contrary to all expectation, the PMP+PC inhibitor system allows a significant boost in the effectiveness of the traditional inhibitor system comprising HQ and PTZ. Similarly, the PMP+PC+dispersant stabilizer system jointly with the traditional HQ+PTZ inhibitor system prevents the unwanted polymer deposition.

The invention claimed is:

1. A method for inhibiting polymerization of ethylenically unsaturated monomers that comprise at least one heteroatom, comprising manufacturing, purifying, storing, and/or transporting such monomers in the presence of at least two phenol derivatives and at least one ancillary polymerization inhibitor which is different from the two phenol derivatives, wherein the two phenol derivatives are para-methoxyphenol and pyrocatechol and the at least one ancillary polymerization inhibitor comprises hydroquinone and phenothiazine as a mixture.

2. The method according to claim 1 wherein the method limits and/or prevents fouling of industrial equipment used in the preparation of the ethylenically unsaturated monomers.

3. The method according to claim 2, wherein the method limits and/or prevents fouling of industrial equipment used during distillation of the ethylenically unsaturated monomers.

4. The method according to claim 1, wherein the amount of the two phenol derivatives is effective to enhance the polymerization-inhibiting effectiveness of the at least one ancillary polymerization inhibitor.

5. The method according to claim 1, wherein the monomers are manufactured, purified, stored, and/or transported in the presence of the at least two phenol derivatives, the at least one ancillary polymerization inhibitor, and, optionally, para-dimethoxybenzene.

6. The method according to claim 1, wherein the two phenol derivatives are para-methoxyphenol and pyrocatechol, and the weight ratio of para-methoxyphenol to pyrocatechol is from 1 to 99.

7. The method according to claim 1, wherein the two phenol derivatives and the at least one ancillary polymerization inhibitor are present in a total amount of from 20 ppm to 1%, relative to the total weight of the monomers, the two phenol derivatives, and the at least one polymerization inhibitor.

8. The method according to claim 1, wherein the monomers are manufactured, purified, stored, and/or transported in the presence of the at least two phenol derivatives, the at least one ancillary polymerization inhibitor, and at least one dispersant.

9. The method according to claim 8, wherein the dispersant is selected from sulfonates, esters, succinimides, tristyrylphenols, acrylates, amides, amines, imidazoline, phenates, phosphates, and mixtures thereof.

10. The method according to claim 1, wherein the ethylenically unsaturated monomers comprising at least one heteroatom are selected from the group consisting of halogenated unsaturated monomers, acrylic monomers, unsaturated acrylic resins, unsaturated amides, unsaturated ethers, and vinylpyridines.

* * * * *